United States Patent [19]

Ray et al.

[11] Patent Number: 5,665,111
[45] Date of Patent: Sep. 9, 1997

[54] METHOD FOR ANCHORING A SURGICAL SUTURE TO BONE

[75] Inventors: Charles D. Ray, Golden Valley; Eugene A. Dickhudt, New Brighton, both of Minn.

[73] Assignee: RayMedica, Inc., Bloomington, Minn.

[21] Appl. No.: 589,739

[22] Filed: Jan. 22, 1996

[51] Int. Cl.⁶ ................................................ A61B 17/00
[52] U.S. Cl. ........................... 606/232; 606/73; 606/83; 128/898
[58] Field of Search ........................ 606/232, 72, 73, 606/75, 79, 80, 83, 86, 103, 104; 128/898

[56] References Cited

U.S. PATENT DOCUMENTS

| | | |
|---|---|---|
| 3,914,801 | 10/1975 | Dick et al. ............................. 3/1 |
| 5,203,787 | 4/1993 | Noblitt et al. ..................... 606/232 |
| 5,306,290 | 4/1994 | Martins et al. ................... 606/232 |
| 5,318,578 | 6/1994 | Hasson ............................. 606/232 |
| 5,336,240 | 8/1994 | Metzler et al. ................... 606/232 |
| 5,356,413 | 10/1994 | Martins et al. ..................... 606/75 |
| 5,372,604 | 12/1994 | Trott ................................. 606/72 |
| 5,411,523 | 5/1995 | Goble .............................. 606/232 |
| 5,417,692 | 5/1995 | Goble et al. ....................... 606/73 |

*Primary Examiner*—Jeffrey A. Schmidt
*Attorney, Agent, or Firm*—Kinney & Lange, P.A.

[57] ABSTRACT

A surgical method and tools for anchoring a suture to bone is disclosed. The method includes forming an opening through a top surface of the bone, positioning a suture within the opening and crimping a region of the top surface of the bone surrounding the opening to anchor the suture within the opening. The tools used with the disclosed surgical method include a punch, a broach, a guide and a swage. The punch and the broach are used to create a uniform diameter opening in the bone by compressing bone material. The guide is used to position a suture, preferably having a shoulder, in the opening. Finally, the suture is used to crimp the region of the top surface of the bone surrounding the opening.

14 Claims, 7 Drawing Sheets

METHOD FOR ANCHORING A SURGICAL SUTURE TO BONE

BACKGROUND OF THE INVENTION

The present invention concerns a method and tools for anchoring a surgical suture to bone. More particularly, it relates to a surgical method which creates a small opening in the bone and utilizes tissue surrounding that opening to anchor a surgical suture to the bone.

Many surgical procedures entail attaching certain objects, such as healing acceleration articles, ligaments or tendons to bone. The vast majority of these surgical attachment procedures requires the use of a surgical suture. Basically, the suture is secured to both the bone and the object in question. The suture is then drawn tight (forcing the object into contact with the bone) and tied. While this method is commonplace, it presents several difficulties.

One of the main problems associated with surgical attachments is the means by which the suture is secured to the bone. Healing acceleration articles, ligaments and tendons are easily pierced by a simple surgical needle. Once pierced, the suture is passed through the hole created by the needle and secured about the object. This simple procedure is not available for bones. Human bones have an outer layer comprised of hard, cortical tissue which is difficult to pierce. In other words, the surgical needle used to penetrate the healing acceleration article, ligament or tendon in question cannot likewise be used to create a hole through a bone.

Several methods and devices have been created in an attempt to overcome the problems associated with securing or anchoring a suture to a bone. For example, surgical drills have been used to drill a hole completely through the bone. The suture is then passed through this hole and tied back on to itself. This approach has several drawbacks. First, the area above the bone to be drilled must be fully exposed to provide adequate space for the drilling device. Further, any tissue, organs, etc., located behind the bone can be damaged when the drill tip passes through the bone. Additionally, excess bone debris projected from the drill bit can cause subsequent damage to areas surrounding the bone. In other words, to create the hole, the drilling procedure removes bone tissue in the form of bone debris. If any of this bone debris becomes lodged in certain areas of the body, harm to the patient can result.

A second approach is the use of suture anchors. Suture anchors come in many different forms, but serve the same basic function. Generally, the anchor has a body machined from surgically-safe material and includes an attachment means by which a suture can be secured to the body. A small hole or opening is drilled into the bone and the anchor body is inserted into that hole. The suture, secured to the anchor by the attachment means, is then effectively mounted to the bone.

Suture anchors can and do assume a variety of forms. For example, as shown in U.S. Pat. No. 5,203,787, a suture anchor can be a pair of barbs inserted into a pre-formed hole in the bone. The barbs project into the bone tissue and act to secure the suture. Alternatively, as described inn U.S. Pat. No. 5,470,354, a bone anchor can assume the shape of a screw which is screwed into the bone. The suture is connected to either the head or body of the screw. Further, as shown in U.S. Pat. No. 5,356,413, a bone anchor can include a main body which is inserted into a drilled hole, along with a plurality of barbs extending therefrom. The barbs are secured to the bone wall and assist in maintaining the position of anchor body. Finally, as shown in U.S. Pat. No. 5,324,308, suture anchors can be a specially designed, wedge shaped body inserted into a pre-drilled hole in the bone.

As evidenced by the number of patents in this area, bone anchors have in no way been perfected. Whatever the form, bone anchors are man-made. In other words, an extraneous material, such as metal, ceramic, etc., is machined to a certain shape and then implanted into the patient's body. While these materials are normally surgically-safe, difficulties and complications can nonetheless occur.

These complications may not develop immediately, but instead can remain latent for several years. As bone anchors are normally permanent attachments, they are not removed from the bone, possibly decomposing and causing harm at some point in the future. While bioabsorbable materials are available to overcome this problem, strength of the anchor is sacrificed. Additionally, bone anchors are inserted into a preformed hole in the bone. Because the bone anchor is composed of material different than the bone, the bone tissue will begin resorbing in the area surrounding the bone anchor. Over time, the bone tissue will actually pull away from the anchor, thus decreasing the anchor's pullout strength. Also, bone anchors are generally designed so that a portion of the anchor body and/or attachment means permanently extends above the normal surface of the bone. This extension can cause complications when other portions of the body unexpectedly contact the protruding anchor. Finally, as with the drilling procedure, bone tissue is removed to create the hole into which the anchor is inserted. Thus, the bone incurs immediate damage further, various stresses on the bone during normal, day-to-day activities can augment this damage.

The necessity for anchoring a suture to a bone during surgery is prevalent. However, the many attempts to create a feasible method of accomplishing this use, such as drilling or bone anchors, have many drawbacks. Therefore, a substantial need exists for a simple method of anchoring a suture to a bone which does not require removal of bone tissue or the implantation of a separate anchoring body.

SUMMARY OF THE INVENTION

The invention provides a method of anchoring a suture to a bone without the use of a separate anchoring body or device. The method includes compressing a small area of the bone to form an opening. One end of a suture is inserted into the opening, after which a top surface of the bone in the region surrounding the opening is swaged or crimped to anchor the suture within the opening and therefore to the bone. By this method, the suture is anchored to the bone via the bone's own tissue. Further, by compressing the bone tissue, as opposed to removing bone tissue, subsequent ingrowth will further anchor the suture to the bone.

The tool kit utilized for accomplishing the above surgical method preferably includes four tools: a punch, a broach, a guide and a swage. The punch has a shank attached to a head which tapers to a tip. The punch has a shank attached to a head which is of a uniform diameter. The guide has a shank attached to a head which is straight and has a diameter which is less than that of the broach head. Finally, the swage has a shank attached to a head which is a hollow cylinder having a conical inner wall.

The punch, via a force applied to the shank, imparts a notch into the surface of the bone. The broach is used to expand the notch into an opening of relatively uniform diameter. The guide positions one end of a suture within this opening. Finally, the swage crimps a region of the top surface of the bone surrounding the opening to anchor the suture within the opening.

In alternative embodiments, several of the above-mentioned tools are combined. For example, the guide and the swage are combined into a single tool. This tool is comprised of a hollow shaft, a guide rod and a locking mechanism. The guide rod is selectively attached within the hollow shaft by the locking mechanism. The hollow shaft has a proximal and a distal end. The distal end of the hollow shaft is wedge shaped to perform the crimping function. The guide rod has a first and second end. The second end of the guide rod assumes a concave shape which is utilized to guide an end of a suture. The locking mechanism provides for a first position in which the second end of the guide rod extends outwardly from the distal end of the hollow shaft. In a second position, the guide rod retracts within the hollow shaft, allowing the hollow shaft to perform the crimping function previously described.

In a further embodiment, all of the above-mentioned tools are combined into a single, suture anchoring device. The suture anchoring device includes a counter-force arm, an action arm and a sequential tool device. The counter-force arm and the action arm are pivotally connected to function in a scissor-like fashion. The sequential tool device is rotatably attached to a leading end of the action arm. The counter-force arm has an anvil positioned opposite the sequential tool device. The sequential tool device has a central body which is circular in shape and from which a punch, a broach, a guide and a swage radially extend.

During use, a surgeon maneuvers the counter-force arm and the action arm to create a working space between the sequential tool device and the anvil large enough to fit around the bone in question. The sequential tool central body is rotated so that the punch is directly above the bone. The counter-force arm and the action arm are forced together, causing the punch to impart a notch into the bone. The punch is removed from the bone and central body is rotated to position the broach above the notch. The arms are forced towards one another, causing the broach to expand the notch into an opening. The broach is retracted from the opening and the central body is rotated so that the guide is directly above the opening in the bone. A suture is placed on the guide which is used to position the suture within the opening in the bone. Finally, the guide is retracted from the opening and the central body is rotated so that the swage is directly above the opening. The arms are then compressed, causing the swage to crimp the top surface of the bone in the region surrounding the opening.

DETAILED DESCRIPTION OF THE PREFERRED EMBODIMENTS

Tool Kit

Figure 1:
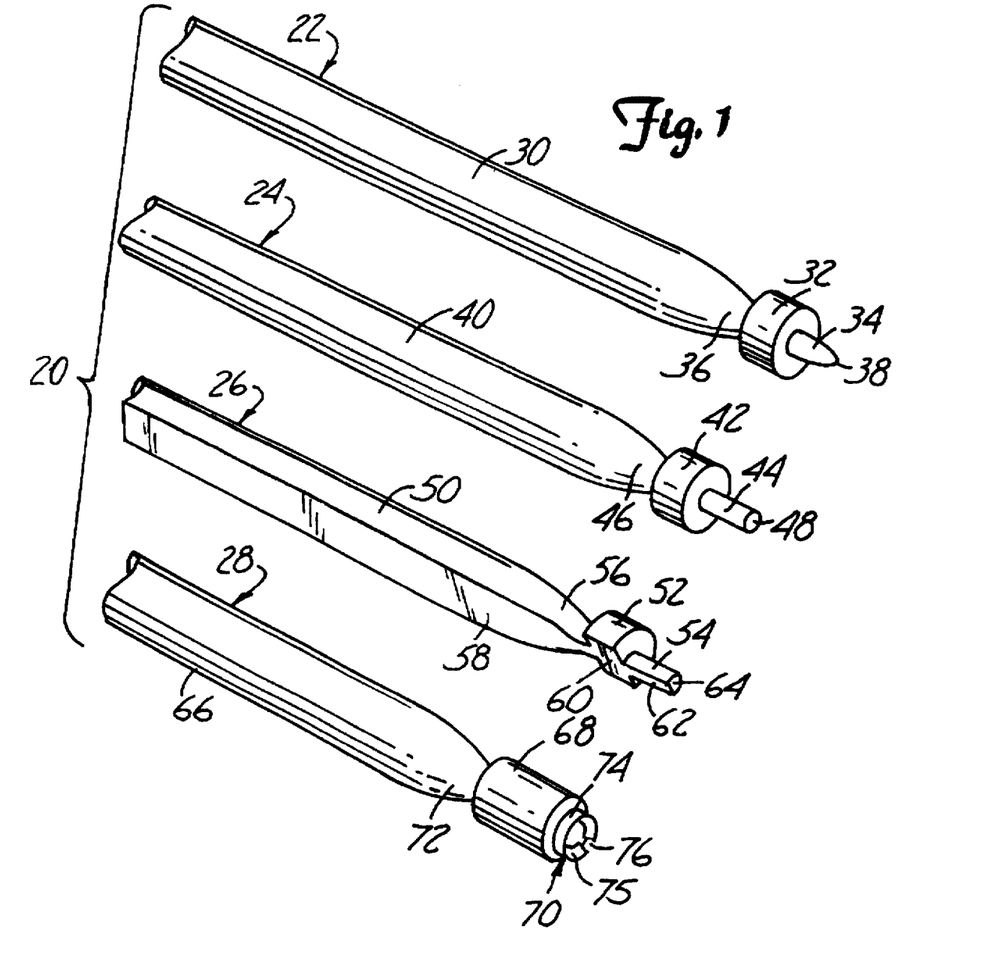
FIG. 1 is a perspective view of a tool kit for anchoring a suture to bone in accordance with the present invention.

A preferred embodiment of a tool kit 20 used to anchor a suture to bone is shown in FIG. 1. The tool kit 20 includes a punch 22, a broach 24, a guide 26 and a swage 28.

The punch 22 includes a shank 30, a stop 32 and a punch head 34. The punch head 34 is integrally attached to a distal end 36 of the shank 30. The punch head 94 is preferably wedge shaped, tapering to a point. The stop 32 is cylindrical in shape, having a central opening sized for frictional attachment to the punch head 34. In this position, the stop 32 extends in a radial fashion from a central axis of the punch head 34.

The broach 24 includes a shank 40, a stop 42 and a broach head 44. The broach head 44 is integrally attached to a distal end 46 of the shank 40. The broach head 44 is preferably a right cylinder, having a relatively uniform diameter and terminates in a flat end 48. In the preferred embodiment, the broach head 44 has a slight taper of about 1 degree from the stop 42 to the flat end 48. The stop 42 is cylindrical in shape, having a central opening sized for frictional attachment to the broach head 44. In this position, the stop 42 extends in a radial fashion from a central axis of the broach head 44.

The guide 26 includes a shank 50, a stop 52 and a guide head 54. The guide head 54 is integrally attached to a distal end 56 of the shank 50. The shank 50 is cylindrical, having a flat side wall 58. Similarly, the stop 52 has a flat side wall 60 and the guide head 54 has a flat side wall 62. The overall configuration of the guide 26 is such that the flat side walls 58, 60, and 62 are aligned. In addition to the flat side wall 62, the guide head 54 has an end 64 which is preferably concave. In the preferred embodiment, the guide head 54 has a slight taper of about 1 degree from the stop 52 to the end 64. The stop 52 has a central opening sized for frictional attachment to the guide head 54.

The swage 28 includes a shank 66, a stop 68 and a swage head 70. The swage head 70 is integrally attached to a distal end 72 of the shank 66. The swage head 70 is a hollow cylinder, having a leading end 73 from which a circular outer wall 74 and a conical inner wall 75 external. By this configuration, the swage head 70 forms a circular wedge. The swage head 70 also includes a notch 76. The stop 68 is cylindrical in shape, having a central opening sized for frictional attachments to the swage head 70. In this position, the stop 68 extends in a radial fashion from a central axis of the swage head 70.

The punch 22, the broach 24, the guide 26 and the swage 28 are all comprised of similar material. For example, the shanks 30, 40, 50 and 66 and the heads 34, 44, 54 and 70 are all machined from surgically safe, stainless steel material. The stops 32, 42, 52 and 68 are also preferably made of stainless steel material, but can be any other stiff material such as hardened rubber. Further, while the stops 32, 42, 52 and 68 are described as being fictionally attached to the respective heads 34, 44, 54 and 70, other forms of attachment, including machining the tool as a single piece, are equally acceptable.

For reasons more fully explained below, the heads 34, 44, 54 and 70 have related dimensions. For example, the maximum diameter of the punch head 34 is the same as the diameter of the broach head 44. The guide head 54 guide has a diameter which is smaller than that of the broach head 44. Conversely, the leading end 73 of the swage head 70 has an inner diameter which is greater than the diameter of the broach head 44. In a preferred embodiment, the diameter of the broach head 44 is 0.0625 inches.

Similarly, the length of each of the heads 34, 44, 54 and 70 is interrelated. More specifically, the length of the punch head 34 (as defined by the stop 32 and the point 38) is the same for the broach head 44 and the guide head 54. The length of the swage head 70 is less than the lengths of the other tool heads 34, 44 and 54. In a preferred embodiment, the punch head 34, the broach head 44 and the guide head 54 have a length in the range of 0.125 to 0.1875 inches, while the swage head 70 has a length in the range of 0.0625 to 0.1875 inches.

Method Of Anchoring Suture To Bone

Figure 2A:
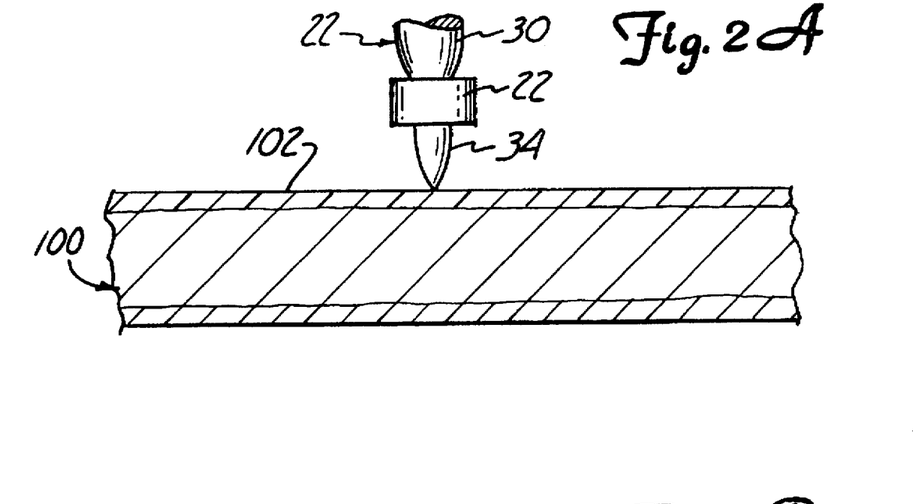
FIGS. 2A–2G illustrate the method of anchoring a suture to bone in accordance with the present invention.

The method of anchoring a suture to bone in accordance with the present invention is shown in FIGS. 2A–2G. First, as shown in FIG. 2A, the punch 22 is positioned over a bone 100 such that the punch head 34 contacts a top surface 102 of the bone 100. With respect to the orientation shown in FIG. 2A, a downward force, via a hammer or similar device, is placed on the shank 30 (shown partially in FIG. 2A), driving the punch head 34 into the bone 100. The actual direction of the force applied to the shank 30 will obviously vary depending upon the orientation of the bone 100. Due to the tapered shape of the punch head 34, the downward force imparts a wedge-shaped notch or opening into the bone 100. The downward motion of the punch 22 continues until the stop 32 contacts the top surface 102 of the bone 100.

Figure 2B:
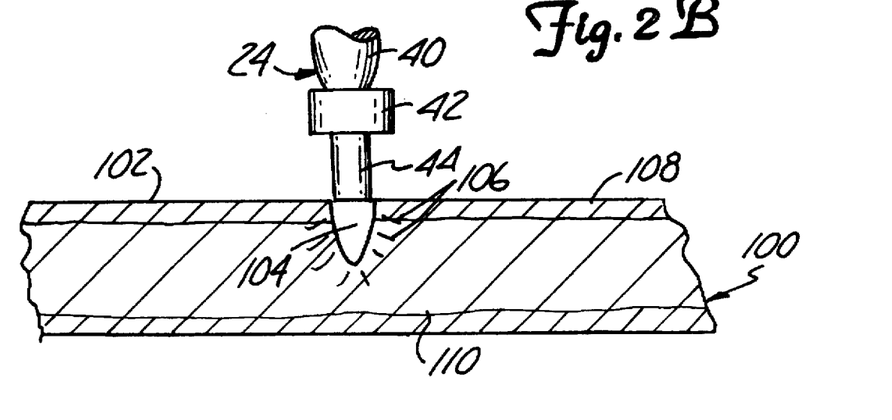

As shown in FIG. 2B, the downward action of the punch 22 creates an opening 104 once the punch head is removed. The opening 104 is defined by compressed bone tissue, as represented by compression lines 106. In other words, bone tissue is compressed, rather than removed, to form the opening 104. The bone 100 is defined by a cortical region 108, comprised of hard bone tissue, and a cancellous region 110, comprised of softer bone tissue. In the preferred embodiment, the opening 104 passes through the cortical region 108 and into the cancellous region 110.

Once the opening 104 is initially formed, the broach 24 is utilized to impart a uniform diameter on the opening 104. More particularly, as depicted in FIG. 2B, the broach head 44 is positioned above the bone 100, over the opening 104. A downward force is applied to the shank 40 (shown partially in FIG. 2B), forcing the broach head 44 into the opening 104. The broach head 44 continues downward until the stop 42 contacts the top surface 102 of the bone 100. As previously described, the length of the broach head 44 corresponds with the length of the punch head 34 (shown in FIG. 2A) and therefore with the length of the opening 104. The downward action of the broach head 44 imparts a uniform diameter on the opening 104. Further, in the preferred embodiment, the broach head 44 has a slight taper so that the broach head 44 can readily be removed from the opening 104.

Figure 2C:
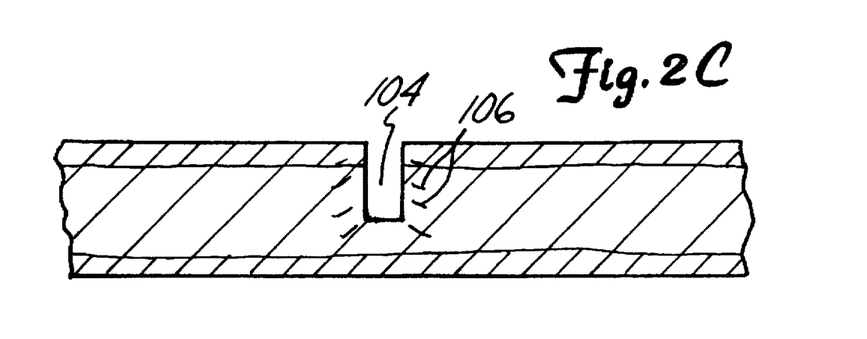

As represented in FIG. 2C, the broaching action results in a relatively uniform opening 104. Once again, the opening 104 has been formed by the compression of bone tissue, as represented by the compressions lines 106.

Figure 2D:
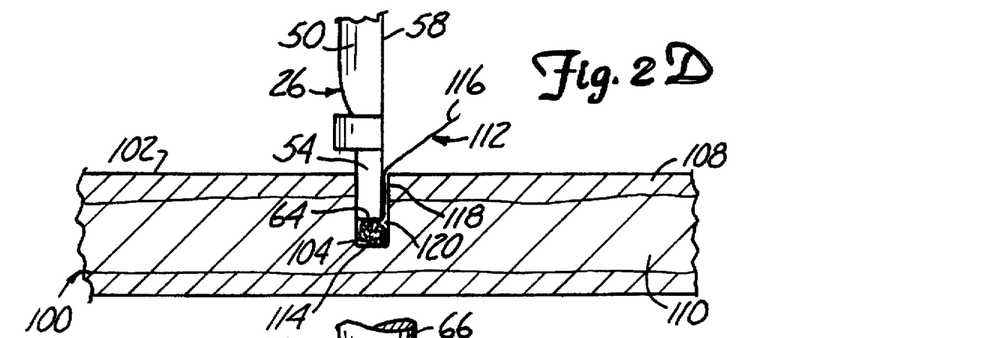

As shown in FIG. 2D, a suture 112 is positioned within the opening 104 by the guide 26. In a preferred embodiment, the suture 112 includes a pre-formed shoulder 114 and a free end 116. As is described in more detail below, the shoulder 114 is preferably a knot. The leading end 64 of the guide head 54 is preferably concave in design to receive the shoulder 114. Further, the guide head 54 has a diameter which is smaller than that of the opening 104 for easy manipulation within the opening 104. The surgeon (not shown) maneuvers the shank 50, and thus the guide head 54, to position the shoulder 114 within the opening 104. In the preferred embodiment, the shank 50 has the flat side wall 58 which provides the surgeon visual access to the opening 104. The free end 116 of the suture 112 is allowed to pass between the guide head 54 and a side wall of the opening 104. As depicted in FIG. 2D, the free end 116 passes outwardly from the top surface 102 of the bone 100.

The opening 104 is defined by an upper portion 118 and a lower portion 120. In general terms, the upper portion 118 corresponds with the cortical region 108, whereas the lower portion 120 corresponds with the cancellous region 110. Preferably, the shoulder 114 is positioned by the guide 26 in the lower portion 120.

Figure 2E:
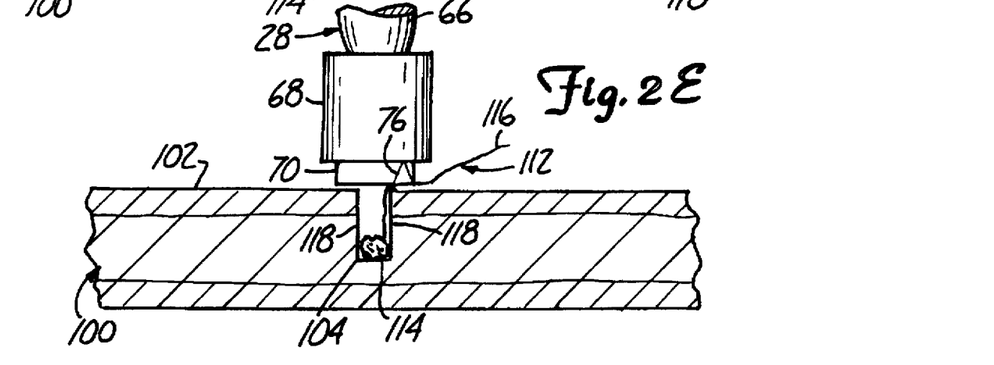

Once the shoulder 114 has been properly positioned within the opening 104, the swage 28 is used to crimp bone tissue in a region surrounding the top portion 118 of the opening 104, as depicted in FIG. 2E. The swage head 70 is positioned centrally above the opening 104 and the free end 116 of the suture 112 is passed through the notch 76. A downward force, via a hammer or similar device, is supplied to the shank 66 causing the swage head 70 to drive into the top surface 102 of the bone 100. The head 70 is driven downward until the stop 68 contacts the top surface 102 of the bone 100. The tapered or wedge shape of the swage head 70 causes the bone tissue in the region surrounding the upper portion 118 of the opening 104 to crimp inward. The swage head 70 will not cut or otherwise damage the suture 112 due to the notch 76.

Figure 2F:
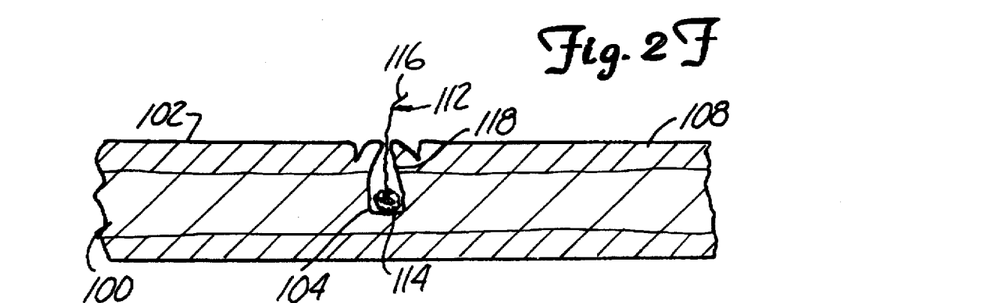

As depicted in FIG. 2F, effectively, the crimping action constricts the upper portion 118 of the opening 104. The shoulder 114 of the suture 112 is maintained within the opening 104, whereas the free end 116 extends outwardly from the top surface 102. Following the crimping action, the diameter of the upper portion 118 is less than the diameter of the shoulder 114. Therefore, when an attempt is made to pull the suture 112 from the opening 104, the shoulder 114 is held or anchored in the opening 104 at the upper portion 118.

In a preferred embodiment, the tissue surrounding the top portion 118 is in the cortical region 108 of the bone 100. Thus, the tissue used to constrict the upper portion 118 of the opening 104 is comprised of hard bone tissue, which will not readily deform or relax to its initial configuration prior to crimping. By utilizing this attribute of the bone 100, the crimped tissue will maintain its constricted position indefinitely.

Figure 2G:
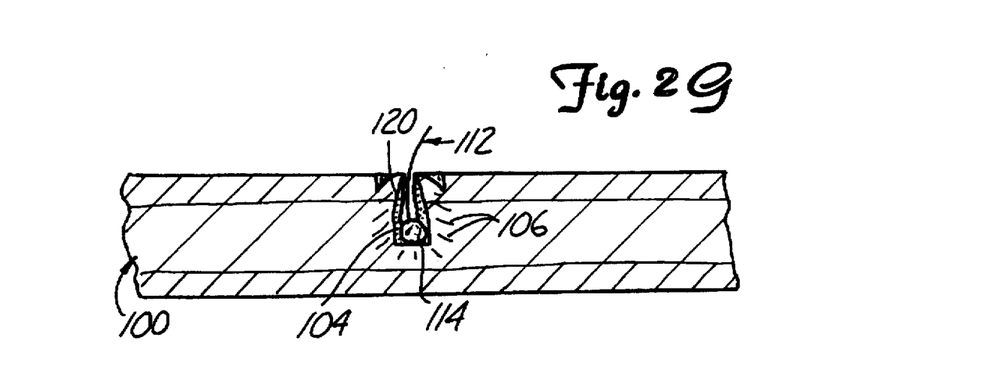

As depicted in FIG. 2G, healing characteristics of the bone 100 further strengthen the anchoring of the suture 112 within the opening 104. As previously described, the opening 104 is created by compressing bone tissue, represented by the compression lines 106. Over time, the tissue will relax, causing the opening 104 to become smaller as the bone tissue expands back to its original position. Further, new bone tissue surrounding the opening 104 will begin to grow. Within 24 hours, callous growth begins to take place, which later becomes bone tissue. Therefore, this bone ingrowth further reduces the size of the opening 104, and increases the pullout strength. As shown in FIG. 2G, bone ingrowth 122 reduces the size of the opening 104 and solidifies the position of the shoulder 114 within the opening 104.

Suture Shoulder 114

Figure 3A:
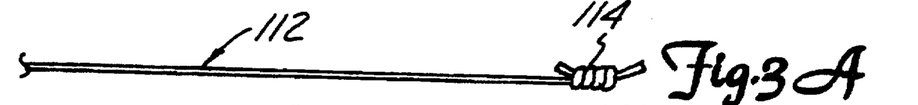
FIGS. 3A–3C are side views of surgical sutures having shoulders formed by alternative embodiments of the present invention.
Figure 3B:
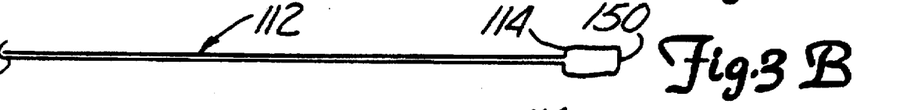
Figure 3C:
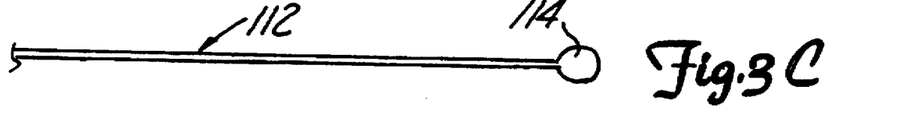

As previously described, the preferred method of anchoring a suture to a bone requires formation of the shoulder 114 on the suture 112. The suture 112 can be made of absorbable or non-absorbable material, depending upon the particular surgical application. In either case, the shoulder 114 can assume a variety of forms, as represented by FIGS. 3A–3C. As depicted in FIG. 3A, the shoulder 114 is simply a knot formed at an end of the suture 112. The shoulder 114 shown in FIG. 3A is formed by tying off an end portion of the suture 112 and cutting away any excess material.

Alternatively, as shown in FIG. 3B, the shoulder 114 is comprised of a peg 130 attached to the suture 112. Alternatively, the peg 130 is encompassed by the suture 112 material. The peg 130 is made of solid, surgically safe material, and cannot easily be deformed.

Finally, as shown in FIG. 3C, the shoulder 114 can be a conglomeration of melted suture 112 material. By slowly melting an end of the suture 112, the shoulder 114 is formed and assumes a spherical shape.

Other methods of forming the shoulder 114 on the suture 112 are equally applicable. The only criteria is that the shoulder 114 have a diameter which is greater than the diameter of the suture 112. In fact, during the suture manufacturing process, the suture 112 can be pre-formed with an enlarged end which will act as the shoulder 114. In a preferred embodiment, the shoulder 114 has a diameter which is four times larger than the suture 112.

Application Of Method Of Anchoring Suture To Bone

Figure 4:
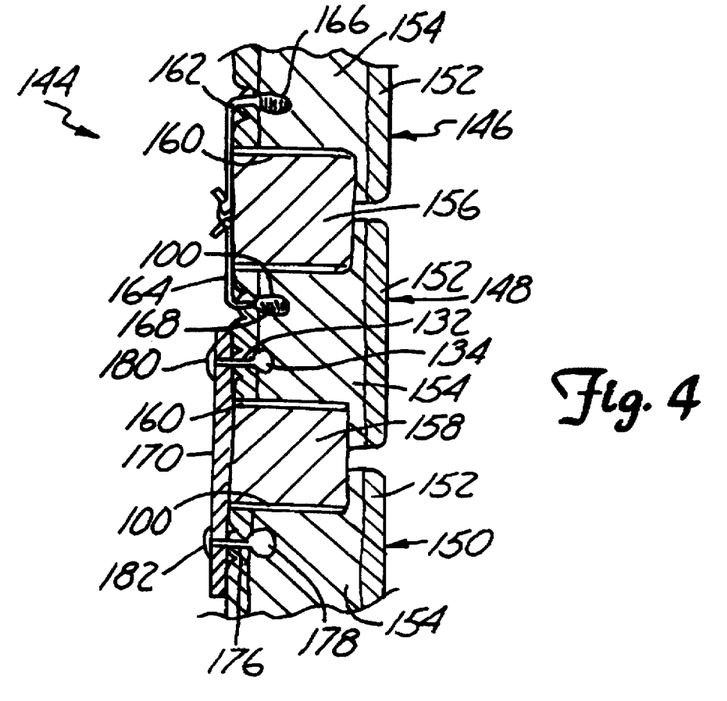
FIG. 4 is a side sectional view of a fused spinal column having surgical sutures anchored to bone in accordance with the present invention.

The method of anchoring suture to bone of the present invention has a wide variety of applications. For example, as shown in FIG. 4, sutures anchored to bone in accordance with the present invention can be used during spinal surgery. FIG. 4 represents two approaches for applying the suture anchoring method of the present invention during cervical spine fusion. A cervical spine 144 can be described as having a first vertebral body 146, a second vertebral body 148 and a third vertebral body 150. Each of the vertebral bodies 146, 148 and 150 has an outer, cortical layer 152 and an inner, cancellous layer 154. To alleviate deterioration of the cervical spine 144, the first vertebral body 146 is fused to the second vertebral body 148 by a first bone graft dowel 156. Similarly, a second bone graft dowel 158 is fused between the second vertebral body 148 and the third vertebral body 150. Normally, fusion material 160 is placed between the interface of the bone graft dowels 156, 158 and the respective vertebral bodies 146, 148 and 150. To facilitate hardening of the fusion material 160, additional support or pressure on the exterior of the bone graft dowels 156 and 158 is required. Two different approaches for applying support are shown in FIG. 4.

The first bone graft dowel 156 is supported by a first suture 162 and a second suture 164. The first suture 162 has a shoulder 166 which is anchored to the first vertebral body 146 in accordance with the method of the present invention. Similarly, the second suture 164 has a shoulder 168 which is anchored to the second vertebral body 148 in accordance with the method of the present invention. Once anchored, the sutures 162 and 164 are tied together and act to support the first bone graft dowel 156.

A second method for facilitating and supporting cervical spine fusion is shown with respect to the second bone graft dowel 158 and involves use of an absorbable plate 170. A first suture 172 having a shoulder 174 is anchored to the second vertebral body 148 in accordance with the method of the present invention. Similarly, a second suture 176 having a shoulder 178 is anchored to the third vertebral body 150 in accordance with the method of the present invention. Once so attached, the first suture 172 is passed through a preformed hole in the absorbable plate 170. Likewise, the second suture 176 is passed through a separate pre-formed hole in the absorbable plate 170. With the absorbable plate 170 firmly held against the second bone graft dowel 158, each of the sutures 172 and 176 are melted to form caps 180 and 182. Upon completion of the melting process, the sutures 172 and 176, which have been anchored in accordance with the method of the present invention, act to hold the absorbable plate 170 in the desired position.

Figure 5:
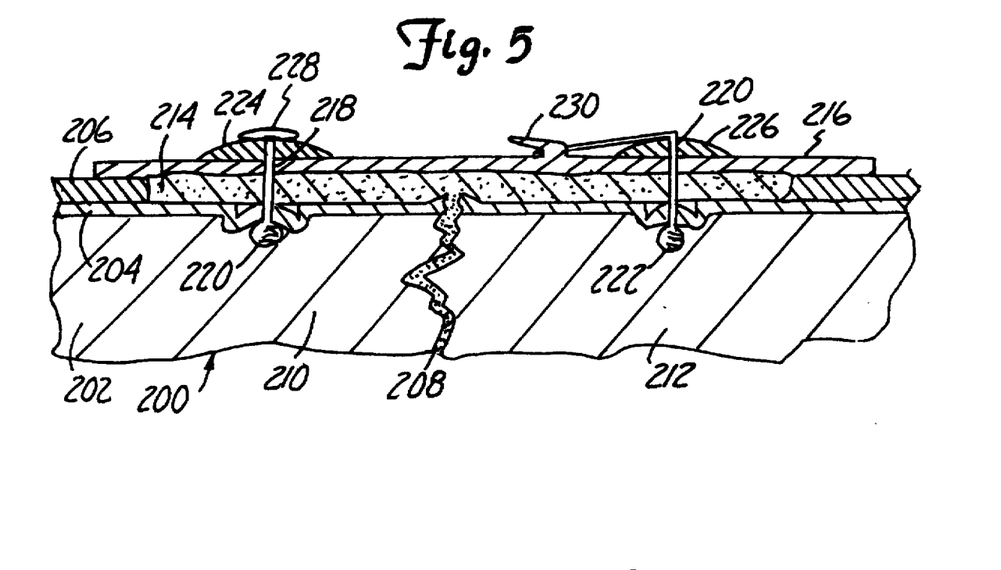
FIG. 5 is a side sectional view of a fractured bone repaired by a device utilizing surgical sutures anchored to bone in accordance with the present invention.

FIG. 5 illustrates use of sutures anchored to bone in accordance with the method of the present invention to support long-bone fusion. A bone 200 comprised of a soft cancellous layer 202, a semi-hard cortex layer 204 and a hard cortex layer 206 is shown in FIG. 5 as being fractured along a fracture line 208. The fracture line 208 divides the bone 200 into a first segment 210 and a second segment 212. To repair the fracture 208, the first segment 210 and the second segment 212 are physically brought together and held in place by a formed graft insert overlay 214. Often times, the formed graft insert overlay 214 must be held in place while it hardens. To facilitate this effect, an absorbable plate 216 is utilized.

The absorbable plate 216 is tightly held against the formed graft insert overlay 214 by a first suture 218 and a second suture 220. Prior to applying the formed graft insert overlay 214, the first suture 218 and the second suture 220 are anchored to the bone 200. In accordance with the method of the present invention, the first suture 218 has a shoulder 221 which is anchored to the semi-hard cortex layer 204 of the first sediment 210. Similarly, the second suture 220 has a shoulder 222 which is anchored to the semi-hard cortex layer 204 of the second segment 212 in accordance with the method of the present invention. The formed graft insert overlay 214 is then disposed over the bone 200 such that the first suture 218 and the second suture 220 projects outwardly therefrom. Finally, the absorbable plate 216 is placed over the formed graft insert overlay 214 as shown in FIG. 5. The absorbable plate 216 has pre-formed holes through which the first suture 218 and the second suture 220 pass.

The absorbable plate 216 is held firmly against the formed graft insert overlay 214 by the first suture 218 and the second suture 220 through a variety of methods, two of which are shown in FIG. 5. The absorbable plate 216 includes a first cap 224 and a second cap 226. The first cap 224 has a hole through which the first suture 218 passes. Likewise, the second cap 226 has a hole through which the second suture 220 passes. The first suture 218 is attached to the absorbable plate 216 by a top 228. The top 228 is formed by melting a free end of the first suture 218. The top 228 engages the first cap 224, thus holding the absorbable plate 214 against the formed graft insert overlay 214.

Alternatively, the absorbable plate 216 includes a cleat 230. After distribution of the form graphed insert overlay 214 and placement of the absorbable plate 216, the second suture 220 is pulled from the second cap 226 to the cleat 230. The second suture 220 is then attached to the cleat 230, effectuating a tight damp between the absorbable plate 216, the formed graft insert overlay 214 and the bone 200.

Whatever the application, the method for anchoring sutures to bone of the present invention provides surgeons with the ability to anchor a suture to a bone without the use external elements. As shown in the two previous examples, the surgical repairs in question do not require the use of any metallic inserts. The absorbable plate(s) and sutures are all designed to safely absorb into the patient's system. Unlike past anchoring methods by which a supplemental anchor, normally made of metal, was permanently attached to a bone, the present method obviates this requirement.

Figure 6A:
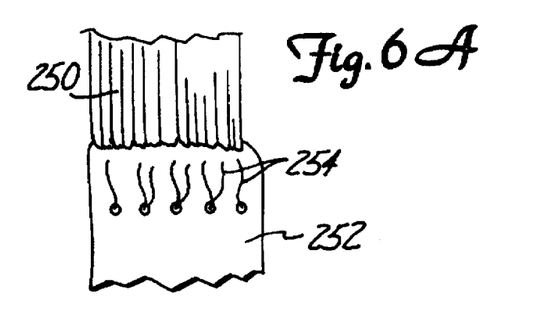
FIG. 6A is a top view of a ligament secured to a bone by surgical sutures anchored to the bone in accordance with the present invention.

In addition to utilizing the method of the present invention to anchor one or two sutures to bone as part of a surgical operation, a series of anchored sutures can be used where a greater holding force is required. For example, as shown in FIG. 6A, the method of the present invention can be used to secure a ligament 250 to a bone 252. Attachment of the ligament 250 to the bone 252 requires a large holding force as, generally speaking, patient movement of the affected area cannot be totally immobilized. Where, for example, the ligament 250 is located in a patient's leg, any movement of that limb will place a great stress on the attachment between the ligament 250 and the bone 252. Therefore, a strong attachment between the ligament 250 and the bone 252 must be provided. To meet this requirement, a series of sutures 254 are used. In accordance with the method of the present invention, each of the series of sutures 254 has a shoulder (256 in FIG. 6B) which is anchored to the bone 252. Once the series of sutures 254 have been anchored, they are tied to the ligament 250. The combined holding force of the series of sutures 254 secures the ligament 250 to the bone 252.

Figure 6B:
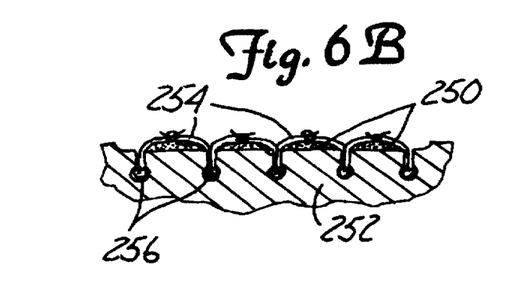
FIG. 6B is a side sectional view of a ligament secured to a bone by surgical sutures anchored to the bone in accordance with the present invention.

As shown in FIG. 6B, the series of sutures 254 are threaded through the ligament 250 and tied. The shoulders 256 are anchored within the bone 252, providing a secure attachment between the ligament 250 and the bone 252. Alternatively, the ligament 250 can be a graft ligament having pre-formed shoulders. These shoulders are inserted into openings in the bone 252 and then anchored via the previously described swaging process.

Alternative Embodiments Of Tools

Figure 7:
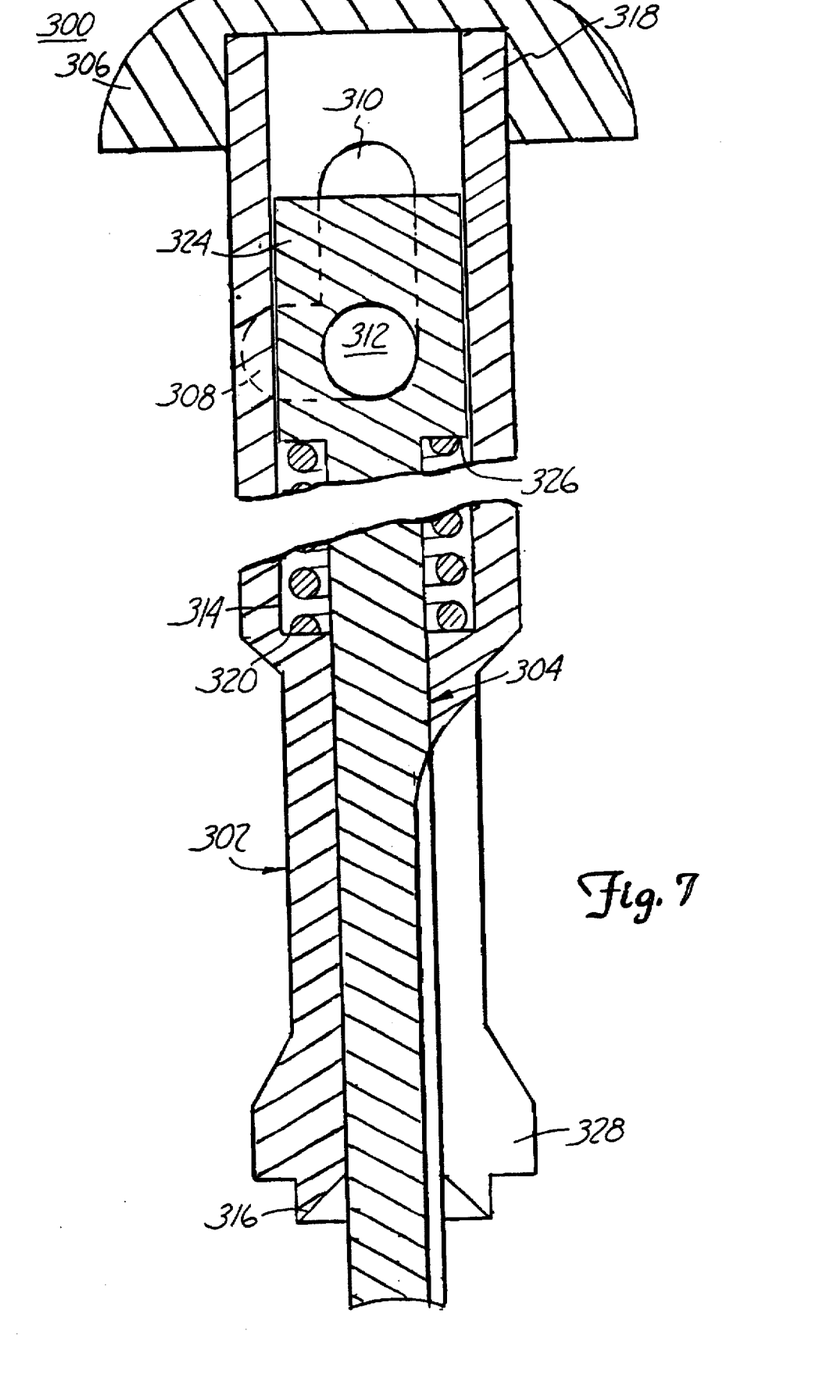
FIG. 7 is a partial side sectional view of an alternative embodiment of a combined guide and swage tool used to anchor a surgical suture to a bone in accordance with the present invention.

As previously described, the tool kit for anchoring suture to bone of the present invention preferably includes four tools. However, several of these tools may be combined into a single tool. For example, as shown in FIG. 7, the guide 26 and the swage 28 (shown in FIG. 1) can be combined into a single tool 300. The combined tool 300 includes a swage shaft 302, a guide rod 304, a knob 306 and a locking mechanism formed by a horizontal slot 308, a vertical slot 310, a pin 312 and a spring 314. The guide rod 304 is selectively connected within the swage shaft 302 by the locking mechanism. The knob 306 is attached to the swage shaft 302.

The swage shaft 302 is hollow, having a distal end 316 and a proximal end 318. The distal end 316 is wedge shaped. The proximal end 318 includes the horizontal slot 308 and the vertical slot 310. Finally, the swage shaft 302 includes a locking wall 320 for receiving a portion of the spring 314.

The guide rod 304 is preferably cylindrical and is of a diameter sized to fit within the swage shaft 302. The guide rod 304 includes a first end 322, a second end 324 and the pin 312. The first end 322 is preferably concave in shape for seating the suture (not shown) during use. The pin 312 is removably attached to the second end 324 and is sized to fit within the horizontal slot 308 and the vertical slot 310 of the swage shaft 302. Finally, the second end 324 of the guide rod 304 includes a receiving wall 326 for receiving a portion of the spring 314.

To assemble the combined tool 300, the spring 314 is placed within the proximal end 318 of the swage shaft 302. When properly positioned, the spring 314 contacts the locking wall 320 of the swage shaft 302. Similarly, the guide rod 304 is disposed into the swage shaft 302, by first removing the pin 312 from the second end 324. The first end 322 is guided into the proximal end 318 of the swage shaft 302 and moved downward toward the distal end 316. The pin 312 is then attached to the second end 324 of the guide rod 304 by passing the pin 312 though either the horizontal slot 308 or the vertical slot 310 in the swage shaft 302. Finally, the knob 306 is placed over the proximal end 318 of the swage shaft 302.

The combined tool 300 has two working positions. In a first working position, the guide rod 304 is maneuvered downward with respect to the swage shaft 302 via a force placed upon the pin 312. The pin 312, which is otherwise attached to the second end 324 of the guide rod 304, passes along the vertical slot 310 in the swage shaft 302. As the guide rod 304 is moved downward, the spring 314 is compressed between the locking wall 320 of the swage shaft 302 and the receiving wall 326 of the guide rod 304. When the guide rod 304 reaches the position shown in FIG. 7, the pin 312 is maneuvered along the horizontal slot 308 (to the left in FIG. 7). Once the pin 312 is located in the horizontal slot 308, the spring 314 acts to maintain the guide rod 304 in this position. More specifically, the spring 314 imparts an upward force on the receiving wall 326 of the guide rod 304. This force, in turn, causes the pin 312 to contact a side of the horizontal slot 308 and maintain the pin 312, and thus the guide rod 304, in this position. In the first working position, the first end 322 of the guide rod 304 extends beyond the distal end 316 of the swage shaft 302. Once so positioned, the first end 322 of the guide rod 304 is used to position a suture within an opening in a bone (not shown) as previously described.

The combined tool 300 also provides for a second working position in which the swage shaft 302 is used to crimp a region of bone surrounding an opening in accordance with the method of the present invention as previously described. The pin 312 is maneuvered in the horizontal slot 308 (rightward in FIG. 7). Once the pin 312 enters the area of interface between the horizontal slot 308 and the vertical slot 310, the pin 312 is allowed to move upward, via expansion of the spring 314, in the vertical slot 310. The pin 312, and therefore the guide rod 304, moves upwards in response to the expansion of the spring 314 until the pin 312 contacts an end wall of the vertical slot 310. In this second position, the first end 322 of the guide rod 304 is retracted within the swage shaft 302, such that the distal end 316 is unobstructed.

Once secured in the second working position, the combined tool 300 is used to crimp bone tissue above an opening in a bone (not shown). Basically, as previously described, the distal end 316 of the swage shaft 302 is positioned over the opening (not shown) and a sharp force is applied to the knob 306. This force causes the distal end 316 of the swage shaft 302 to crimp the region of bone surrounding the opening (not shown). In a preferred embodiment, the swage shaft 302 includes a stop 328 which prevents the swage shaft 302 from projecting into the bone beyond a desired level.

Figure 8:
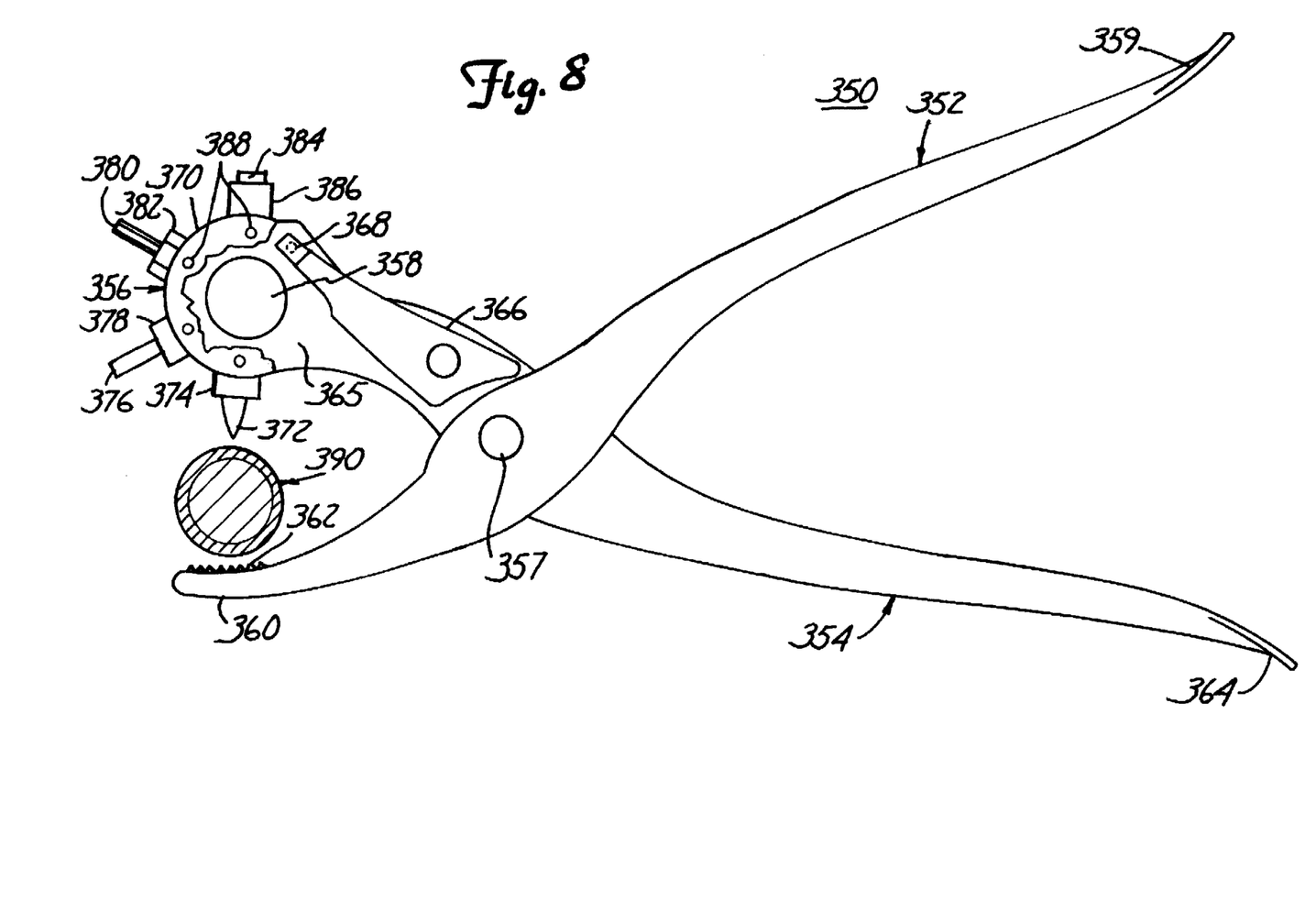
FIG. 8 is a side view of an alternative embodiment of a surgical tool used to anchor a surgical suture to a bone in accordance with the present invention.

A second alternative embodiment of a combined tool of the present invention combines the punch 22, the broach 24, the guide 26 and the swage 28 (shown in FIG. 1). A suture anchoring device 350 is shown in FIG. 8. The suture anchoring device 350 includes a counterforce arm 352, an action arm 354 and a sequential tool device 356. The counterforce arm 352 and the action arm 354 are pivotally coupled by a pin 357. The sequential tool device 356 is rotatably attached to the action arm 354 by a pin 358.

The counterforce arm 352 includes a grip end 359 and a force end 360 to which an anvil 362 is attached.

The action arm 354 includes a grip end 364, a leading end 365 and a spring housing 366. The spring housing 366 has an indexing stop pin (not shown) which extends perpendicularly into a pin receiving opening 368 in the leading end 365.

The sequential tool device 356 includes a central body 370, a punch 372 having a stop 374, a broach 376 having a stop 378, a guide 380 having a stop 382 and a swage 384 having a stop 386. The punch 372, the broach 376, the guide 380 and the swage 384 are attached to and extend radially from the central body 370, which is cylindrical. Finally, the central body 370 includes a plurality of pin holes 388. The plurality of pin holes 388 are positioned on the central body 370 to receive the indexing stop pin (not shown) and lock the central body 370 in place with respect to the leading end 365 of the action arm 354.

During use, the grip end 359 of the counterforce arm 352 and the grip end 364 of the action arm 354 are separated to create a working space between the sequential tool device 356 and the anvil 362. The working space thusly created is sized in accordance with the bone 390 to which a suture (not shown) is to be anchored. The bone 390 shown in FIG. 8 can be a small round bone, such as an arm, leg, finger, rib or a larger bone such as a vertebra or a femur. Depending upon the particular surgical application, the force end 360 of the counterforce arm 352 can be alternatively shaped to provide an appropriate working space.

The sequential tool device 356 is rotated until the punch 372 is directly above the anvil 362 and therefore the bone 390. Once in this position, the spring housing 366 is maneuvered to pass the indexing pin (not shown) through the pin receiving opening 368 in the leading end 365 of the action arm 354 and through one of the plurality of holes 388 in the central body 370. The indexing pin functions to lock the sequential tool device 356 in the desired position.

Once properly positioned, the grip ends 359 and 364 are forced towards one another, pivoting the counterforce arm 352 and the action arm 354 on the pin 357 and causing the punch 372 and the anvil 362 to contact opposite sides of the bone 390. As the grip ends 359 and 364 are forced even further, the punch 372 imparts a notch or opening (not shown) in the bone 390. The punch 372 continues inward until the stop 374 contacts the bone 390. At this point, the grip ends 358 and 364 are separated, removing the punch 372 from the bone 390. The spring housing 366 is maneuvered to remove the indexing pin from the central body 370. The central body 370 is then rotated (counterclockwise in FIG. 8) until the broach 376 is directly above the anvil 362 and therefore the opening (not shown) in the bone 390. The spring housing 366 is then replaced such that the indexing pin (not shown) falls into one of the plurality of holes 388 in the central body 370, locking the sequential tool device 356 in place. Once again, the grip ends 359 and 364 are brought together so that the broach 376 broaches the opening (not shown) previously created by the punch 372.

The same process is repeated for the guide 380 and the swage 384. As previously described, the guide 380 and the swage 384 position the suture (not shown) and anchor it to the bone 390.

The method and tools of the present invention provide a simple, yet highly effective approach for anchoring a suture to bone. By creating a small opening through the cortical region of the bone, inserting a suture into the opening, and then crimping a top portion of the opening, a suture can be anchored to a bone without the use of separate, possibly harmful bodies anchor or damaging surgical procedures in which bone tissue is removed. The present method utilizes the bones own tissue to anchor the suture. Further, by compressing instead of removing bone tissue, the present method exploits the ingrowth healing characteristics of the bone to strengthen the anchor over time. As with the surgical method, the tools of the present invention are straightforward and easy to use.

Although the present invention has been described with reference to preferred embodiments, workers skilled in the art will recognize that changes may be made in form and detail without departing from the spirit and scope of the present invention. For example, the method steps of using a punch to form a notch or opening in the bone and using a broach to expand the notch into an opening of uniform diameter can be combined. With this combination, the opening in the bone is formed with a single step by a single tool. Notably, it is not required to broach the opening to a uniform diameter. Similarly, while a guide tool has preferably been provided to assist a surgeon in positioning a suture within the opening, the surgeon can accomplish this step manually, without the aide of a guide tool.

The opening formed in the bone has been described as extending slightly below the cortical layer and preferably having a diameter of about 0.0625 inches. These general guidelines are not limitations. In other words, the opening need not extend entirely through the cortical region. On the other hand, if desired, the opening can extend entirely through the bone. Similarly, the opening can have a larger or smaller diameter. The only limitation is that the diameter of the opening must be greater than the diameter of the suture to be anchored. Further, while the opening has been depicted as extending perpendicular to the surface of the bone, the opening can be orientated in an angular fashion. In fact, in certain applications, as angular orientated opening will provide a larger holding force.

The method of the present invention has been described to preferably include crimping a top portion of the bone in a region surrounding the opening, so as to anchor a shoulder of a suture within the opening. In this regard, it is not necessary to crimp only cortical bone tissue. The crimping may further include cancellous bone tissue. Thus, the swage tool can assume a variety of shapes. For example, the swage head can be corrugated to effectuate a plurality of crimped bone regions. Further, the swage head can be longer so as to crimp cancellous bone tissue. Finally, the swage head need not encompass the entire opening. In other words, the swage head can be much smaller and applied at numerous locations around the circumference of the opening to achieve the desired crimping effect. Similarly, the swage head can be designed to constrict the opening even further than has been described in the preferred embodiments. With this approach, the suture need not have a shoulder. Instead, the bone tissue is crimped directly on to the circumference of the suture itself.

What is claimed is:

1. A surgical method for anchoring a suture, having a first end and second end, to a bone having a top surface, the method including:

forming an opening in the bone through the top surface;

positioning the first end of the suture within the opening such that the second end of the suture extends from the opening; and crimping a region of the top surface of the bone surrounding the opening to secure the first end of the suture within the opening.

2. The surgical method of claim 1 wherein the suture has a first diameter, the method further including:

forming a shoulder on the first end of the suture, wherein the shoulder has a second diameter which is greater than the first diameter and is positioned within the opening.

3. The surgical method of claim 2 wherein forming a shoulder includes creating a knot on the first end of the suture.

4. The surgical method of claim 2 wherein forming a shoulder includes melting the first end of the suture.

5. The surgical method of claim 2 wherein forming a shoulder includes attaching a peg to the first end of the suture.

6. The surgical method of claim 2 wherein the opening is defined by an upper portion and a lower portion, and further wherein positioning the first end of the suture within the opening includes positioning the shoulder below the upper portion of the opening.

7. The surgical method of claim 6 wherein crimping the region surrounding the opening includes crimping the upper portion of the opening to a diameter which is less than the second diameter.

8. The surgical method of 2 wherein positioning the first end of the suture within the opening includes positioning the shoulder below the top surface.

9. The surgical method of claim 1 wherein the top surface of the bone is cortical tissue.

10. The surgical method of claim 1 wherein forming an opening includes compressing bone tissue.

11. The surgical method of claim 1 wherein forming an opening includes:

creating a notch in the top surface of the bone; and expanding the notch to uniform diameter.

12. The surgical method of claim 1 wherein the opening is cylindrical.

13. The surgical method of claim 1 wherein the bone has a thickness and the opening has a length which is less than the thickness of the bone.

14. The surgical method of claim 1 wherein crimping a region of the top surface of the bone includes crimping a circular pattern into the top surface.

* * * * *